(12) United States Patent
Uttenthal

(10) Patent No.: US 8,461,115 B2
(45) Date of Patent: Jun. 11, 2013

(54) METHODS FOR LOCAL TREATMENT WITH FACTOR VII

(75) Inventor: Lars Otto Uttenthal, Salamanca (ES)

(73) Assignee: Stellaris Pharmaceuticals ApS, København (DK)

( * ) Notice: Subject to any disclaimer, the term of this patent is extended or adjusted under 35 U.S.C. 154(b) by 593 days.

(21) Appl. No.: 12/282,908

(22) PCT Filed: Mar. 16, 2007

(86) PCT No.: PCT/DK2007/000132
§ 371 (c)(1),
(2), (4) Date: Oct. 20, 2008

(87) PCT Pub. No.: WO2007/104317
PCT Pub. Date: Sep. 20, 2007

(65) Prior Publication Data
US 2009/0093410 A1  Apr. 9, 2009

(51) Int. Cl.
| A61K 38/36 | (2006.01) |
| A61K 35/14 | (2006.01) |
| A61P 11/00 | (2006.01) |
| C07K 14/745 | (2006.01) |

(52) U.S. Cl.
USPC ......... 514/13.5; 514/14.3; 530/380; 530/384; 424/94.64

(58) Field of Classification Search
None
See application file for complete search history.

(56) References Cited

U.S. PATENT DOCUMENTS

| 4,235,871 | A | 11/1980 | Papahadjopoulos et al. |
| 4,501,728 | A | 2/1985 | Geho et al. |
| 4,784,950 | A | 11/1988 | Hagen et al. |
| 4,837,028 | A | 6/1989 | Allen |
| 5,180,583 | A | 1/1993 | Hedner |
| 5,374,617 | A | 12/1994 | Morrissey et al. |
| 5,788,965 | A | 8/1998 | Berkner et al. |
| 5,824,639 | A | 10/1998 | Berkner |
| 5,874,407 | A | 2/1999 | Kelley et al. |
| 5,997,864 | A | 12/1999 | Hart et al. |
| 6,806,063 | B2 | 10/2004 | Pedersen et al. |
| 6,825,323 | B2 | 11/2004 | Hess |
| 6,905,683 | B2 | 6/2005 | Persson et al. |
| 6,911,323 | B2 | 6/2005 | Persson et al. |
| 6,960,657 | B2 | 11/2005 | Persson et al. |
| 2002/0192271 | A1 | 12/2002 | Hedner et al. |
| 2004/0120993 | A1 | 6/2004 | Zhang et al. |
| 2008/0188400 | A1* | 8/2008 | Ropke et al. ............ 514/2 |

FOREIGN PATENT DOCUMENTS

| EP | 0225160 A2 | 11/1986 |
| JP | 116213 | 7/1984 |
| WO | WO 93/06855 | 4/1993 |
| WO | WO 93/15234 | 8/1993 |
| WO | WO 93/23074 | 11/1993 |
| WO | WO 00/28065 | 5/2000 |
| WO | WO 01/85198 | 11/2001 |
| WO | WO 02/29084 | 4/2002 |
| WO | WO 03/037932 | 5/2003 |
| WO | WO 03/039584 | 5/2003 |
| WO | WO 2004/083361 | 9/2004 |
| WO | WO 2005/072700 | 8/2005 |
| WO | WO 2005/074975 | 8/2005 |
| WO | WO 2006/005340 | 1/2006 |
| WO | WO 2006/026998 | 3/2006 |

OTHER PUBLICATIONS

Bulletti, C., et al. 1997 Annals of the NY Academy of Sciences 828: 285-290.*
Ahonen J and Jokela R, (2005) Recombinant factor VIIa for life-threatening post-partum haemorrhage, British Journal of anaesthesia, 94 (5): 592-5.
Anderson, JM and Etches D (2007) "Prevention and Management of Postpartum Hemorrhage", American Family Physician, vol. 75, No. 6, 875-882.
Baksu, Alparslan, Kalan, Aysel, Ozkan, Arzu, Baksu, Basak, Tekelioglu, Meltem and Goker, Nimet (2005), "The effect of placental removal method and site of uterine repair on postcearean endometritis and operative blood loss", Acta Obstetricia et Gynecologica Scandinavica, 84:3, 266-269.
Bouvmeester FW, Jonkhoff AR, Verheijen RH, van Geijn HP. "Successful treatment of life-threatening postpartum hemorrhage with recombinant activated factor VII". Obstet Gynecol. Jun. 2003;101(6):1174-6.
Brice A, Hilbert U, Roger-Christoph S, Fernandez H, Dumenil AS, Descorps-Decléere A, Mercier F, Benhamou D. "Recombinant activated factor VII as a life-saving therapy for severe postpartum heamorrhage unresponsive to conservative traditional management" Ann Fr Anesth Reanim. Nov. 2004;23(11):1084-8.
Doumouchtsis, S Papageorghiou, AT and Arulkumaran S, (2007), "Systematic Review of Conservative Management of Postpartum Hemorrhage: What to Do When Medical Treatment Fails", Obstetrical and Gynecological Survey, vol. 62, No. 8.
Gidiri M, Noble W, Rafique Z, Patil K and Lindow SW (2004) 'Caesarean section for placenta praevia complicated by postpartum haemorrhage managed successfully with recombinant activated human coagulation Factor VIIa', Journal of Obstetrics and Gyneacology, 24:8, 925-926.
Heilmann L, Wild C, Hojnacki B and Pollow K, (2006) "Successful Treatment of Life-threatening Bleeding after Cesarean Section with Recombinant Activated Factor VII", Clin Appl Thromb Hemost, 12 (2); 227-229.
Jimeâ Nez-Yuste A, Villar A, Morado M, Canales M, M. Herna Â Ndez MC, Sanjurjo MJ, Quintana M and Herna Â Ndez-Navarro F (2000), "Continuous infusion of recombinant activated factor VII during caesarean section delivery in a patient with congenital factor VII deficiency", Haemophilia, 6, 588-590.

(Continued)

Primary Examiner — Marsha Tsay
(74) Attorney, Agent, or Firm — Licata & Tyrrell P.C.

(57) ABSTRACT

The present invention provides methods for the local treatment of bleeding in a subject and/or reducing unwanted effects associated with the systemic administration of thrombotic agents to a subject, by local administration of FVII to the subject.

24 Claims, No Drawings

OTHER PUBLICATIONS

Kominiarek, MA, Kilpatrick, SJ (2007) "Postpartum Hermorrhage: A Recurring Pregnancy Complication" Semin Perinatol 31:159-166.

Merminod T, Pellicciotta S and Bounameaux H, (2006) "Limited usefulness of D-dimer in suspected deep vein thrombosis of the upper extremities" Blood Coagulation and Fibrinolysis, 17:225-227.

Price G, Kaplan J and Skowronski G, (2004) "Use of recombinant factor VIIa to treat life-threatening non-surgical bleeding in a post-partum patient", British Journal of Anaesthesia, 93 (2): 298-300.

Segal S, Shemesh IY, Blumenthal R, Yoffe B, Laufer N, Ezra Y, Levy I, Mazor M and Martinowitz U (2003), "Treatment of obstetric hemorrhage with recombinant activated factor VII (rFVIIa)" Arch Gynecol Obstet, 268:266-267.

Shamsi TS, Hossain N, Soomro N, Hasan JA, Noorani M, Kazi S, Quraishy MS, Jameel B, Sultan ST, Haider S. Use of recombinant factor VIIa for massive postpartum haemhorrage: case series and review of literature. J Pak Med Assoc. Nov. 2005; 55(11):512-5.

Sobieszczyk, Slawomir, Breborowicz, Grzegorz H, Platicanov, Viliyan, Tanchev, Stoyan and Kassler, Graig M. (2006) "Recombinant factor VIIa in the management of postpartum bleeds: an audit of clinical use", Acta Obstetricia et Gynecologica Scandinavica, 85:10, 1239-1247.

Szoka et al. Comparative properties and methods of preparation of lipid vesicles (liposomes). Ann. Rev. Biophys. Bioeng 9:467-508 (1980).

Verre M, Bossio F, Mammone A, Piccirillo M, Tancioni F, Varano M. "Use of recombinant activated factor VII in a case of severe postpartum heamorrhage". Minerva Ginecol. Feb. 2006;58(1): 81-4.

Zupancic Salek S, Sokolic V, Viskovic T, Sanjug J, Simic M, Kastelan M (2002), "Successful Use of Recombinant Factor VIIa for Massive Bleeding after Caesarean Section due to HELLP Syndrome", Acta Haematol; 108:162-163.

Thachil, J. and Toh, C.-H. "Disseminated Intravascular Coagulation in Obstetric Disorders and its Acute Haematological Management" Blood Reviews 2009 23:167-176.

Tuffnell, D. J. "Amniotic Fluid Embolism" Current Opinion in Obstetrics and Gynecology 2003 15:119-122.

Communication Under R. 71(3) EPC from EP App No. 07711275.3-2107 with pending claims, Nov. 17, 2011, EPO.

* cited by examiner

METHODS FOR LOCAL TREATMENT WITH FACTOR VII

This patent application is the National Stage of International Application No. PCT/DK2007/000132, filed Mar. 16, 2007, which claims the benefit of priority from U.S. Provisional Patent Application Ser. No. 60/782,914, filed Mar. 16, 2006, teachings of each of which are herein incorporated by reference in their entirety.

All patent and non-patent references cited in the present application, are also hereby incorporated by reference in their entirety.

FIELD OF INVENTION

The present invention provides methods to arrest clinically significant local hemorrhage of whatever cause, including but not limited to, intrauterine hemorrhage, such as postpartum hemorrhage, hemorrhage following cesarean section, persistent or recurrent hemorrhage such as hemorrhage due to uterine fibroids or other uterine neoplasias; hemorrhage caused by bone or joint surgery, such as allopathic surgery or arthroscopic surgery; peritoneal hemorrhage, for example in tertiary peritonitis; hemorrhage caused by liver resection; hemorrhage due to pulmonary surgery, like lung resection or decortications of the parietal pleura; skin necrectomy after second and third degree burns; hemorrhage caused by cardiovascular surgery, for example implantation of an artificial aorta, endoarterial embolization of bleeding vessels; hemorrhage caused by sternotomy, esophageal bleeding of a varicose vein; hemorrhage due to prostate surgery; hemorrhage in head, throat, nose, ears and mouth; hemorrhage due to microsurgery of the middle ear; acute hemorrhage, chronic hemorrhage and acute on chronic hemorrhage, including hemorrhage due to congenital or acquired deficiency of one or more blood coagulation factors. By "clinically significant" in this context is meant a duration and rate of blood loss that on presentation requires, or if not arrested will foreseeably require, the transfusion of whole blood or packed red blood cells to maintain the health and life of the patient suffering that blood loss. In the methods of the present invention, activated blood coagulation factors, i.e. hemostatic agents, are administered directly to the bleeding site. These methods are useful in clinical medicine, for example in the fields of surgery. The methods of the present invention are especially useful in the fields of obstetrics and gynecology. These methods are also relevant to the fields of hematology, rheumatology, transplantation medicine, infectious diseases and oncology.

BACKGROUND OF INVENTION

Previous treatments for local bleeding comprise surgical and medical approaches. Among surgical approaches, local lesions can sometimes be treated by excision, cauterization, ligation or tamponation, but this applies only to restricted numbers and classes of lesions. Among medical approaches, the most common is the systemic administration of blood platelets and/or blood coagulation factors, of which the patient may have a congenital or acquired deficiency, and/or the systemic administration of inhibitors of fibrinolytic (clot-dissolving) mechanisms. The latter include tranexamic acid, which inhibits the conversion of plasminogen to the fibrinolytic enzyme plasmin, and aprotinin, which inactivates fibrinolytic enzymes. The disadvantage of these medical approaches is that their effect is often inadequate to arrest the local bleeding, especially if this is caused by a combination of one or more local lesions and a generalized deficiency of one or more hemostatic mechanisms or due to an affection of the capillary membrane either of primary, unknown etiology or secondary to an identifiable systemic disease or condition, such as bone marrow transplantation, chemotherapy, systemic autoimmune disease or infection. The inhibition of fibrinolysis can only arrest bleeding if the hemostatic mechanisms are adequate to form a blood clot in the first place.

Local bleeding is typically a medical emergency, in which rapid arrest of bleeding is required, often allowing insufficient time to identify the underlying causes with certainty, and in which treatment of the underlying disease is too retarded in comparison with the acute life-threatening hemorrhage. Medical treatments are therefore often given speculatively and without certainty of their efficacy in the individual patient, but with the intention of avoiding or delaying the need for a more radical surgical intervention to arrest the bleeding.

SUMMARY OF INVENTION

In one aspect, the present invention relates to a method for arresting local bleeding in a subject, whether the bleeding be acute or recurrent or chronic or acute on chronic, of whatever cause, which comprises local administration of Factor VII to the subject. In one preferred aspect the present invention relates to a method for arresting uterine and more preferred intrauterine bleeding.

Accordingly, the invention relates to the use of a blood coagulation factor for the manufacture of a medicament for the treatment or prevention of acute or recurrent or chronic bleeding in a subject, wherein said medicament is administered locally by various means.

An advantage of the present invention is that unwanted side effects or insufficient therapeutic effects of the systemic administration of thrombotic and/or hemostatic agents are reduced or avoided.

DETAILED DESCRIPTION OF THE INVENTION

The present invention relates to the local administration to a subject, preferably a mammal, more preferably a human, most preferably a female human, of purified or concentrated human FVII or biologically active derivatives or analogues or homologues of the same, or recombinant FVII, however prepared, and especially activated human factor VII, to arrest local bleeding, not including tracheal, bronchial or alveolar bleeding or hemoptysis. Such bleeding may result from an acute condition, a recurrent condition or a chronic condition and can be localized in any part of the human body. Preferably the bleeding is localized in the uterus. The bleeding may be caused by or associated with a disease or may result from or be associated with surgery or any other injury.

Definitions

When used herein the term "blood coagulation factor" includes all such proteinaceous factors, including, but not limited to, factor VII, factor VIII, factor IX, factor V, factor XI, factor XIII, and any combination thereof.

When used herein, the term "factor VII" or "FVII) is intended to encompass factor VII polypeptides in their uncleaved (zymogen) form, as well as those that have been proteolytically processed to yield their respective bioactive forms, which may be designated factor VIIa. The complete nucleotide and amino acid sequence for human factor VII are known, see U.S. Pat. No. 4,784,950, FIGS. 1 and 2a and 2b. Typically, factor VII is cleaved between residues 152 and 153 to yield factor VIIa. When used herein in connection with factor VIIa, the term "variant" includes, without limitation, factor VII polypeptides that have either been chemically modified relative to human factor VIIa and/or contain one or more amino acid sequence alterations (such as 20 or fewer, for example 17 or fewer, such as 15 or fewer, for example 13 or fewer, such as 11 or fewer, for example 9 or fewer, such as 7 or fewer, for example 5 or fewer, such as 3 or fewer, for example 2 or fewer, such as 1 or fewer) amino acid substitutions, deletions, inversions, or additions relative to human factor VIIa. Such variants may exhibit different properties relative to human factor VIIa, including stability, phospholipid binding, altered specific activity, and the like. A factor VIIa variant includes polypeptides that exhibit at least about 10%, preferably at least about 30%, more preferably at least about 50%, and most preferably at least about 70%, of the specific biological activity of human factor VIIa. For purposes of the invention, factor VIIa biological activity may be quantified by measuring the ability of a preparation to promote blood clotting using factor VII-deficient plasma and thromboplastin, as described, e.g., in U.S. Pat. No. 5,997,864. In this assay, biological activity is expressed as the reduction in clotting time relative to a control sample and is converted to "factor VII units" by comparison with a pooled human serum standard containing 1 unit of factor VII activity per ml. Alternatively, factor VIIa biological activity may be quantified by (i) measuring the ability of factor VIIa or a factor VIIa equivalent to produce activated factor X in a system comprising tissue factor embedded in a lipid membrane and factor X. Non-limiting examples of factor VIIa variants and the measurement of their biological activity have been set forth in WO2005074975, which is hereby incorporated by reference in its entirety. Further non-limiting examples of factor VIIa variants are polypeptides having greater than 50 percent sequence identity, and preferably greater than 90 percent sequence identity (such as greater than 91% sequence identity, for example greater than 92% sequence identity, such as greater than 93% sequence identity, for example greater than 94% sequence identity, such as greater than 95% sequence identity, for example greater than 96% sequence identity, such as greater than 97% sequence identity, for example greater than 98% sequence identity, such as greater than 99% sequence identity, for example greater than 99.5% sequence identity), to human factor VIIa.

It is further understood that Factor VII molecules suitable for use in the present invention may be chemically derivatized or altered, for example, peptides with non-natural amino acid residues (e.g., taurine residue, beta- and gamma-amino acid residues and D-amino acid residues), C-terminal functional group modifications, such as amides, esters, and C-terminal ketone modifications and N-terminal functional group modifications, such as acylated amines, Schiff bases, or cyclization, such as found, for example, in the amino acid pyroglutamic acid, or the Factor VII molecule may be linked to polyethyleneglycol (PEG) chains.

The blood factor VII is preferably purified and/or concentrated, and may e.g. be prepared from plasma or by means of recombinant DNA technology including expression in cell culture or transgenic animals or may be prepared synthetically.

By the terms "factor XIII" and "activated factor XIII" are meant the blood coagulation factor XIII and its activated forms as described in WO9315234, which is hereby incorporated by reference in its entirety. For convenience, the activated forms of factor XIII, factor XIII a'a and factor XIII a'a', are individually or collectively referred to as factor XIIIa. When used herein in connection with factor XIIIa, the term "variant" includes biologically active forms of factor XIIIa having at least about 10%, preferably at least about 30%, more preferably at least about 50%, and most preferably at least about 70%, of the specific biological activity of human factor XIIIa in an assay such as described by Dvilansky et al. (1970). Non-limiting examples of variants are polypeptides having at least 75% sequence identity to activated human factor XIII, such as at least 85% sequence identity, e.g. at least 90% sequence identity, such as at least 95% sequence identity, e.g. at least 96% sequence identity, such as at least 98% sequence identity, e.g. at least 99% sequence identity to activated human factor XIII.

It is to be understood, that the terms "bleeding" and "hemorrhage" are used interchangeably in this application.

Indications

In one embodiment the methods of the present invention are used for the treatment of intrauterine hemorrhage, which may be due to conditions including, but not limited to: first-trimester abortions including spontaneous incomplete abortion, cervical ectopic pregnancy or interstitial ectopic pregnancy; second-trimester abortions including spontaneous incomplete abortion, non-invasive or invasive hydatidiform mole, or choriocarcinoma; third-trimester premature and mature deliveries with complications such as lateral, marginal, partial or total placenta previa, accrete or percrete placenta, retention of the placenta or placental cotyledon, uterine atonia, amniotic embolism, septicemia and hemolysis or hemolysis due to other causes, fibrinolytic disorders and disseminated intravascular coagulation (DIC); postpartum hemorrhage of unknown origin or due to retention of membranes or cotyledons, endometritis, uterine fibroids or uterine malformations; anovulation uterine hemorrhage either juvenile or due to endometrial hyperplasia; uterine fibroids; menopausal and post-menopausal hemorrhage; oncologic conditions such as cervical or endometrial cancers, either primary or with recurrence in the vaginal vault, ovarian cancer with recurrence in the vaginal vault; and per-operative hemorrhage associated with hysterectomy, radical hysterectomy with lymph-node sampling or exairesis, excision of tumor deposits in the pelvic wall, bowels and deep pelvic compartments; and stages 3 and 4 of pelvic endometriosis.

For example, is it believed that the methods of the present invention will be useful in treating postpartum hemorrhage, severe postpartum bleeding after cesarean section, severe intrauterine bleeding due to hemolysis, elevated liver enzymes, and low platelets (HELLP) syndrome, disseminated intravascular coagulation (DIC), hereditary deficiency of blood coagulation factor VII, Glanzmann's thrombasthenia, von Willebrand's disease, Borgschulte-Grigsby combined deficiency of blood coagulation factors II, VII, IX and X.

In one embodiment the methods of the present invention will be useful in treating bone and/or joint bleeding, such as for example bleeding caused by or associated with bone or joint surgery, including but not limited to, alloplastic surgery or arthroscopic surgery.

In another embodiment the bleeding treated according to the methods of the present invention is peritoneal hemorrhage, caused by or associated with conditions including, but not limited to, tertiary peritonitis.

In a further embodiment the bleeding is an abdominal bleeding, such as a bleeding relating to surgical events.

In a further embodiment the bleeding treated according to the present invention is liver bleeding. In another embodiment the liver bleeding is caused by or associated with liver resection.

In one embodiment of the present invention the bleeding is a pulmonary bleeding. In a further embodiment the pulmonary bleeding is caused by or associated with pulmonary surgery, selected from the group consisting of, but not limited to: lung resection or decortication of the peritale pleura.

In yet another embodiment the bleeding treated according to the methods of the present invention is skin bleeding, such as bleeding caused by or associated with skin necrotomy. In a further embodiment of the present invention the skin necrotomy is associated with second and/or third degree burns.

In a preferred embodiment the method of the present invention is used for treating cardiovascular bleeding. In another embodiment of the present invention the cardiovascular bleeding is caused by or associated with cardiovascular surgery, including, but not limited to, implantation or embolization. In a further embodiment of the present invention the implantation is an implantation of an artificial aorta. In a preferred embodiment of the present invention the embolization is an endoarterial embolization.

In another embodiment the methods of the present invention are used for treatment of bleeding caused by or associated with sternotomy.

In one embodiment the bleeding treated according to the methods of the present invention is esophageal bleeding. In another embodiment the esophageal bleeding is bleeding of a varicose vein is.

In a further embodiment the methods of the present invention are used for treatment of prostate bleeding. In another embodiment of the present invention the prostate bleeding is caused by or associated with prostate surgery, including, but not limited to, prostate resection.

The methods of the present invention are also useful for treatment of bleeding in the head, such as bleeding selected from the group consisting of, but not limited to: bleeding in nose, ears or mouth. Examples of such bleedings include, but are not limited to, nosebleed, bleeding caused by or associated with nose surgery, ear surgery or oral surgery, like for example tooth-extraction. In another embodiment the bleeding treated according to the methods of the present invention is bleeding of the middle ear. The methods of the present invention are also useful in treating hemorrhage due to microsurgery of the middle ear. Furthermore, bleeding in connection with craniotomy may also be treated according to the invention.

Administration

The present invention relates to local administration of FVII. Methods of administration include but are not limited to the use of factor VII in the form of a spray, net, bandage, powder, sponge, granule, plaster, film, swap, gel, paste, compress and/or a solution comprising factor VII.

Accordingly, in one embodiment methods of administration include, but are not limited to, spraying, lavage, flushing or installation, using as fluid a physiologically acceptable composition in which the blood coagulation factor or factors have been dissolved.

In another embodiment the factor VII is administered by local application of a gel or paste, in which the factor VII has been dissolved. For example the Gel may be sprayed on the local bleeding site or a gel net may be used for local administration. The gel may be administered to the bone channel and/or the bone surface, for example during or after sternotomy and/or alloplastic and/or arthroscopic surgery.

In relation to administration to uterus, the methods include for example uterine lavage or uterine flushing or uterine instillation according to methods well known to those skilled in the art.

Thus, in one embodiment of the present invention factor VII is administered intrauterine. Such administration can for example be given via incision in the uterus or via a tube in the cervical channel. In a preferred embodiment the incision in the uterus is associated with a caesarean section.

In a further embodiment of the present invention factor VII is administered to the intact uterus. In one non-limiting example, a catheter bearing near its outlet an inflatable balloon of about 100 ml capacity is inserted into the uterine cavity and the balloon inflated with sterile isotonic saline to seal off the uterine cavity at the isthmic or cervical level. The uterine cavity is then washed with 50 ml of sterile physiologically compatible fluid in which the blood coagulation factor or factors has or have been dissolved. This lavage may be repeated at short intervals until the hemorrhage ceases.

In another embodiment of the present invention factor VII is administered to the not intact uterus. In one non-limiting example, a surgical swab is soaked with 50 ml of sterile physiologically compatible in which the blood coagulation factor or factors has or have been dissolved, and used to compress the bleeding site. This procedure is repeated at short intervals until the hemorrhage ceases. After uterine repair a catheter with a 100-ml inflatable balloon can be placed in the cavity for follow-up lavage as described for the intact uterus.

Administration of coagulation factors by the intrauterine route for the treatment of intrauterine bleeding in the intact uterus or by direct local application in the case of a non-intact uterus according to the present invention provides a useful new addition to the methods of treating such bleeding. Furthermore, intrauterine or local administration of coagulation factors is expected to avoid the potential unwanted thrombotic effects of systemic administration of coagulation factors such as recombinant human activated factor VII (rhFVIIa), whose intravenous use is potentially associated with a significant incidence of thrombosis.

A preferred embodiment of the present invention comprises local intrauterine administration to human patients with postpartum hemorrhage of rhFVIIa by means of intrauterine instillation of a physiologically compatible fluid, which in its simplest form can be 50 ml of isotonic saline, in which a suitable dose (e.g. at least 4.8 mg) of rhFVIIa has been dissolved, if necessary supplemented with a suitable dose (e.g. 625 U) of human blood coagulation factor XIII or activated factor XIII dissolved in the same fluid. This administration is repeated at intervals depending on the persistence of intrauterine bleeding. The same compositions can be applied by direct compression with a surgical swab in the case of the non-intact uterus. The intervals of administration by uterine lavage or direct application with a surgical swab is empirically decided by the treating surgeon and may be as short as 5 minutes and as long as 15 or 20 minutes, but may typically be about 10 minutes.

For administration to other areas a variety of administration forms may be used. For example in one embodiment the factor VII is administered as flushing of the bone channel. In a further embodiment the factor VII id administered as intraarticular flushing. Factor VII may also be administered as intraperitoneal flushing. Also flushing in the lung, for example flushing of decorticated lung surface or flushing after resection is in the scope of the present invention.

In another embodiment a net comprising factor VII is placed on the bleeding site, like a tissue surface after surgery, for example on the resection surface after resection, such as a liver or a lung resection or on the skin after necrectomy or any other local bleeding site.

In another embodiment of the present invention factor VII is administered to the bleeding site as a spray, such as for example an aerosolized powder or solution or gel. In a further embodiment the spray is administered to decorticated lung surface and/or resection surface and/or the skin. In an preferred embodiment the spray comprising factor VII is administered to the skin after necrectomy.

Also the factor VII can be administered locally with a medical device coated with a pharmaceutical composition comprising factor VII. For example a spiral used for embolization and/or a balloon and/or a prothesis coated with a composition comprising factor VII may be used for administration. Preferably the prothesis is an aortic prothesis or a joint prothesis.

Possible treatment modalities include the use of a solution of the blood coagulation factor, preferably factor VIIa or biologically active variant thereof, as a first line of treatment by the methods described above, followed by the conventional treatment modalities listed below; the use of said solution as a first line of treatment by pelvic lavage or packing with soaked surgical swabs in situations with profuse bleeding of any cause during surgery; the use of said solution as a first line of treatment in cases with severe bleeding, such as severe uterine bleeding and/or in cases in which packing of the vaginal vault is needed.

The purified or concentrated human blood coagulation factors that are intended to be administered in this way comprise in principle any of the proteinaceous coagulation factors, more preferably a coagulation factor necessary for local intrauterine hemostasis, and most preferably activated factor VII, or a biologically active variant thereof, and/or a blood coagulation factor that promotes clot strength and resistance to fibrinolysis, such as factor XIII or factor XIIIa or a biologically active variant thereof. The blood coagulation factors are preferably purified and/or concentrated, and may e.g. be prepared from plasma or by means of recombinant DNA technology including expression in cell culture or transgenic animals.

Administration of coagulation factors by the intrauterine route for the treatment of intrauterine bleeding in the intact uterus or by direct local application in the case of a non-intact uterus according to the present invention provides a useful new addition to the methods of treating such bleeding. Furthermore, intrauterine or local administration of coagulation factors is expected to avoid the potential unwanted thrombotic effects of systemic administration of coagulation factors such as recombinant human activated factor VII (rhFVIIa), whose intravenous use is potentially associated with a significant incidence of thrombosis.

A preferred embodiment of the present invention comprises local intrauterine administration to human patients with postpartum hemorrhage of rhFVIIa by means of intrauterine instillation of a physiologically compatible fluid, which in its simplest form can be 50 ml of isotonic saline, in which a suitable dose (e.g. at least 4.8 mg) of rhFVIIa has been dissolved, if necessary supplemented with a suitable dose (e.g. 625 U) of human blood coagulation factor XIII or activated factor XIII dissolved in the same fluid. This administration is repeated at intervals depending on the persistence of intrauterine bleeding. The same compositions can be applied by direct compression with a surgical swab in the case of the non-intact uterus. The intervals of administration by uterine lavage or direct application with a surgical swab is empirically decided by the treating surgeon and may be as short as 5 minutes and as long as 15 or 20 minutes, but may typically be about 10 minutes.

In the above treatments, any or all of the conventional treatment modalities for local hemorrhage are expected to be applied before, simultaneously or immediately following the treatment of the present invention; these treatment modalities include the intravenous administration of uterotonic agents, antifibrinolytic agents such as tranexamic acid or aprotinin or plasminogen activator inhibitor 1 (PAI-1), fresh frozen plasma, blood platelets, fibrinogen, human serum albumin and physiologically compatible crystalloid fluids. The coagulation status of the patient is monitored by means of the blood coagulation profile tests available to provide background information. The treatment with a blood coagulation factor that is not factor XIII or factor XIIIa may be combined with application of factor XIII or factor XIIIa, and optionally also with antifibrinolytic agents.

As supplementary or combinatorial treatments, the same coagulation factors can be given intravenously, preferably in the same or similar doses.

An aspect of the present invention and its preferred embodiment is the optional administration of human factor XIII or factor XIIIa, e.g. prepared from plasma or by means of recombinant DNA technology including expression in cell culture or transgenic animals, as supplementary therapy to stabilize the clot already formed as a consequence of factor VIIa that has been locally applied to the uterus. With respect to this adjuvant therapy, the factor XIII or factor XIIIa may be applied locally by the methods specified above or may be administered intravenously.

Preparation of Factor VII

Factor VII may be purified from blood or plasma or Factor VII may be produced recombinantly. A variety of methods for producing Factor VII has been published. See for example WO 00 28065 for high efficiency release of recombinant FVII from eucaryotic cells, and WO 02 29084 for large-scale production of recombinant FVII.

Pharmaceutical Compositions

Pharmaceutical compositions or formulations for use in the present invention include a factor VIIa preparation in combination with, preferably dissolved in, a pharmaceutically acceptable carrier, preferably a carrier or diluent. The pharmaceutical composition may be a solid, a liquid, a gel or an aerosol. The pharmaceutical composition can for example be a spray, a solution or a powder. The carrier may be a gel, a paste, a solid or an aqueous carrier. The gel may be for example be used in the form of a film, a spray or as amorphous gel. The gel preferably is a hydrogel. The solid carrier will preferably be a powder, sponge, granule, plaster, film, a surgical swab or compress or bandage or net. A variety of aqueous carriers may be used, such as 0.9% saline, buffered saline, physiologically compatible buffers and the like. The compositions may be sterilized by conventional techniques well known to those skilled in the art. The resulting aqueous solutions may be packaged for use or filtered under aseptic conditions and freeze-dried, the freeze-dried preparation being dissolved in a sterile aqueous solution prior to administration.

The pharmaceutically acceptable carrier will typically be made of natural macromolecules such as gelatine, collagen, alginic acid, cellulose, chitin, fibrinogen, fibrin, fibrin split products, fibronectin, fibronectin fragments, globulin, myoglobulin, casein, keratin, albumin, polysaccharides e.g. dextranes, glycosaminoglycans, agar, pectin, starch or from chemical modified natural molecules such as denatured gelatine, alginicacid-alginates e.g. calcium alginate, oxidized cellulose, substituted cellulose ethers e.g. glycol cellulose, methyl cellulose, ethyl cellulose, hydroxymethyl cellulose, hydroxyethyl cellulose, hydroxypropylmethyl cellulose, substituted cellulose esters e.g. acetylated cellulose, substituted cellulose ether-esters e.g. acetylated ethyl cellulose, chitosan or from synthetic polymers such as vinyl polymers, e.g. polyacrylic acid, polymethacrylic acid, polyvinyl pyrrolidone and polyvinyl alcohol, polyglycolic acid, polylactic acid, polydextroses or copolymers such as polyoxyethylene-polyoxypropylene copolymers or from natural fibers, synthetic fibers or mixtures of any of the above materials/compounds.

The carrier may furthermore contain a fibrinolysis inhibitor, such as aprotinin, epsilon-aminocaproic acid or tranexamic acid. It may also contain a stabilizer, such as naturally occurring amino acids, mono- or disaccharides, polyglycols, glycerol, proteins or a metal salt, such as calcium salts, and mixtures thereof. Also buffering salts may be added, such as alkaline metal acetates, alkaline metal carbonates or hydrogen carbonates, alkaline metal citrates, alkaline metal phosphates or hydrogen phosphates, alkaline metal succinates, imidazole, TRIS, and zwitteranionic buffering systems, and mixtures thereof. Furthermore, antimicrobial or bacteriostatic agents, such as antibiotics, sulphonamides, antimycotic agents, antiviral compounds, and preservatives may be added.

Solid carriers will typically be selected from those already used as hemostats such as modified cellulose, collagen, gelatine, alginate or synthetic polymers.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc. The formulations may contain pharmaceutically acceptable carriers and excipients including microspheres, liposomes, microcapsules, nanoparticles or the like. Conventional liposomes are typically composed of phospholipids (neutral or negatively charged) and/or cholesterol. The liposomes are vesicular structures based on lipid bilayers surrounding aqueous compartments. They can vary in their physiochemical properties such as size, lipid composition, surface charge and number and fluidity of the phospholipids bilayers. The most frequently used lipid for liposome formation are: 1,2-Dilauroyl-sn-Glycero-3-Phosphocholine (DLPC), 1,2-Dimyristoyl-sn-Glycero-3-Phosphocholine (DMPC), 1,2-Dipalmitoyl-sn-Glycero-3-Phosphocholine (DPPC), 1,2-Distearoyl-sn-Glycero-3-Phosphocholine (DSPC), 1,2-Dioleoyl-sn-Glycero-3-Phosphocholine (DOPC), 1,2-Dimyristoyl-sn-Glycero-3-Phosphoethanolamine (DMPE), 1,2-Dipalmitoyl-sn-Glycero-3-Phosphoethanolamine (DPPE), 1,2-Dioleoyl-sn-Glycero-3-Phosphoethanolamine (DOPE), 1,2-Dimyristoyl-sn-Glycero-3-Phosphate (Monosodium Salt) (DMPA), 1,2-Dipalmitoyl-sn-Glycero-3-Phosphate (Monosodium Salt) (DPPA), 1,2-Dioleoyl-sn-Glycero-3-Phosphate (Monosodium Salt) (DOPA), 1,2-Dimyristoyl-sn-Glycero-3-[Phospho-rac-(1-glycerol)] (Sodium Salt) (DMPG), 1,2-Dipalmitoyl-sn-Glycero-3-[Phospho-rac-(1-glycerol)] (Sodium Salt) (DPPG), 1,2-Dioleoyl-sn-Glycero-3-[Phospho-rac-(1-glycerol)] (Sodium Salt) (DOPG), 1,2-Dimyristoyl-sn-Glycero-3-[Phospho-L-Serine] (Sodium Salt) (DMPS), 1,2-Dipalmitoyl-sn-Glycero-3-[Phospho-L-Serine] (Sodium Salt) (DPPS), 1,2-Dioleoyl-sn-Glycero-3-[Phospho-L-Serine] (Sodium Salt) (DOPS), 1,2-Dioleoyl-sn-Glycero-3-Phosphoethanolamine-N-(glutaryl) (Sodium Salt) and 1,1',2,2'-Tetramyristoyl Cardiolipin (Ammonium Salt). Formulations composed of DPPC in combination with other lipid or modifiers of liposomes are preferred e.g. in combination with cholesterol and/or phosphatidylcholine.

Long-circulating liposomes are characterized by their ability to extravasate at body sites where the permeability of the vascular wall is increased. The most popular way to produce long circulating liposomes is to attach hydrophilic polymer polyethylene glycol (PEG) covalently to the outer surface of the liposome. Some of the preferred lipids are: 1,2-Dipalmitoyl-sn-Glycero-3-Phosphoethanolamine-N-[Methoxy (Polyethylene glycol)-2000] (Ammonium Salt), 1,2-Dipalmitoyl-sn-Glycero-3-Phosphoethanolamine-N-[Methoxy (Polyethylene glycol)-5000] (Ammonium Salt), 1,2-Dioleoyl-3-Trimethylammonium-Propane (Chloride Salt) (DOTAP).

Possible lipid applicable for liposomes are supplied by Avanti, Polar lipids, Inc, Alabaster, Ala. Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028, all of which are incorporated herein by reference. One method is described in example 9. Another method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powderlike form. This film is covered with an aqueous solution of the targeted drug and the targeting component and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

Micelles are formed by surfactants (molecules that contain a hydrophobic portion and one or more ionic or otherwise strongly hydrophilic groups) in aqueous solution.

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127 (Wyandotte Chemicals Corp.). Preferred surfactants are nonionic polyoxyethylene and polyoxypropylene detergents compatible with IV injection such as, TWEEN-80., PLURONIC F-68., n-octyl-.beta.-D-glucopyranoside, and the like. In addition, phospholipids, such as those described for use in the production of liposomes, may also be used for micelle formation.

In some cases, it will be advantageous to include a compound, which promotes delivery of the active substance to its target.

Preferably the pharmaceutical composition permits, that the factor VII stays in contact with the bleeding site. A preferred pharmaceutical composition leads to a increased binding to TF and/or an increased absorption and/or binding to the local tissue and/or protects factor VII from degradation.

In a ready-to-use product incorporation of FVII into the carrier material may be done by various known methods, such as co-precipitation, swelling, dispersion, mixing, soaking, spraying, embedding, injection or a combination thereof.

If the carrier is a gel or a paste, FVII is preferably incorporated into the carrier material under aseptical conditions. This may be carried out by adding a suitable solution of FVII to the carrier material which is then stirred gently by suitable means to obtain a uniform distribution of FVII within the gel or paste. The FVII loaded carrier material is then transferred to a suitable package form e.g. a tube, a plastic container or a syringe. Terminal sterilization may be carried out by means of, for instance, heat or ionizing irradiation.

If the carrier is solid it may be loaded with FVIIa by placing the material in a suitable solution of FVIIa for a period sufficient to ensure that the carrier material is adequately soaked with the FVIIa solution. FVIIa may also be incorporated into the solid carrier by means of spraying, embedding or multiple injections. After vacuum drying or freeze drying to evaporate excess of water the FVIIa impregnated carrier is transferred to a suitable package, such as paper bags or a blister package and terminally sterilized by means of, for instance, heat, ethyleneoxide or ionizing irradiation.

FVIIa may also be added to the carrier just before use, e.g. by spraying a suitable solution of FVIIa onto the carrier material for by embedding the carrier into a FVIIa solution. Alternatively, the FVIIa solution may be injected into the carrier.

Dosing Regimes

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred μg active ingredient per administration with a preferred range of from about 0.1 μg to 10000 μg per kilo body weight. Using monomeric forms of the compounds, the suitable dosages are often in the range of from 0.1 μg to 5000 μg per kilo body weight, such as in the range of from about 0.1 μg to 3000 μg per kilo body weight, and especially in the range of from about 0.1 μg to 1000 μg per kilo body weight. Using multimeric forms of the compounds, the suitable dosages are often in the range of from 0.1 μg to 1000 μg per kilo body weight, such as in the range of from about 0.1 μg to 750 μg per kilo body weight, and especially in the range of from about 0.1 μg to 500 μg per kilo body weight such as in the range of from about 0.1 μg to 250 μg per kilo body weight. Administration may be performed once or may be followed by subsequent administrations. A preferred dosage would be from about 0.1 to about 5.0 mg, preferably from about 0.3 mg to about 3.0 mg, such as from about 0.5 to about 1.5 mg and especially in the range from 0.8 to 1.0 mg per administration. The dosage will also depend on the route of administration and will vary with the age, sex and weight of the subject to be treated. A preferred dosage of multimeric forms would be in the interval 1 mg to 70 mg per 70 kg body weight.

Medical Packaging

The compounds used in the invention may be administered alone or in combination with pharmaceutically acceptable carriers or excipients, in either single or multiple doses. The formulations may conveniently be presented in unit dosage form by methods known to those skilled in the art.

It is preferred that the compounds according to the invention are provided in a kit. Such a kit typically contains an active compound in dosage forms for administration. A dosage form contains a sufficient amount of active compound such that a desirable effect can be obtained when administered to a subject.

The benefits of the present invention are expected to include a reduction of blood loss in the hemorrhagic conditions described, resulting in a lower morbidity and mortality from these conditions; a reduction in the unwanted effects of systemic administration of blood coagulation factors, such as thrombosis; a reduction in the need for additional hemostatic emergency procedures such as arterial embolization, ligation of the internal iliac or ovarian arteries, placement of external uterine compression sutures, or hysterectomy.

EXAMPLES

Example 1

A patient with abdominal bleeding is treated with intraabdominal lavage with fluid containing recombinant activated factor seven in a dose of 20-100 μg/kg body-weight or more dissolved in 200-500 ml sterile isotonic saline or more. The treatment may be repeated in intervals of 20-30 minutes or more until hemostasis is obtained. Similar activated coagulation factors or intra-abdominally placement of biodegradable sponge or foam impregnated with recombinant activated factor seven or similar activated coagulation factors or aerosol spray or spray of a powder formulation with recombinant activated factor seven or similar activated coagulation factors or packing with serviettes impregnated with recombinant activated factor seven or similar activated coagulation factors, where a single dose of FVIIa of 20-100 μg/kg or more is used. The treatment may be repeated in 20-30 minutes intervals or more until hemostasis is obtained.

Example 2

A woman with post partum bleeding secondary to cesarean section or following vaginal delivery is treated with biodegradable sponge or foam impregnated with recombinant activated factor seven or similar activated coagulation factors or intrauterine lavage with fluid containing recombinant activated factor seven or similar activated coagulation factors all, i.e. foam, sponge, and/or lavage fluid is administered either via the cervical route using a catheter with an inflatable balloon to keep the dissolved drug in the intrauterine space for 10-30 minutes or more until hemostasis is obtained or during caesarian section surgery via the transuterine route directly into the uterine cavity where a lavage of FVIIa is dissolved in a volume of 100 ml isotonic saline or more where a dose of FVIIa in a dose of 20-50 μg/kg bodyweight or more is dissolved. The treatment may be repeated in intervals of 20-30 minutes or more 2-3 times or more until hemostasis is obtained Example 3

A patient undergoing post burn necrectomy with surgical resection of second or third degree burn skin tissue and underlying tissue is treated during and post surgery with either lavage fluid containing recombinant activated factor seven or similar activated coagulation factors or biodegradable sponge impregnated with recombinant activated factor seven or similar activated coagulation factors or aerosol spray or spray of a powder formulation with recombinant activated factor seven or similar activated coagulation factors all placed directly on the bleeding denuded tissue after necrectomy. The dose of FVIIa used is 20-50 μg/kg bodyweight per/m$^2$ body surface or more where the FVIIa is applied. The treatment may be repeated in intervals of 20-30 minutes 2-3 times or more.

Example 4

A patient undergoing craniotomy with intracerebral surgery and local bleeding from brain tissue is treated with lavage with fluid containing recombinant activated factor seven or similar activated coagulation factors or local placement of a biodegradable sponge impregnated with recombinant activated factor seven or similar activated coagulation factors or local aerosol spray or spray of a powder formulation with recombinant activated factor seven or similar activated coagulation factors. A dose of 2.5-10 µg/kg bodyweight or more is used. Depending on hemostasis the treatment may be repeated 2-3 times or more in intervals of 20-30 minutes or more until sufficient hemostasis is obtained.

Example 5

A patient with esophageal bleeding due to ruptured varicose veins or traumatic lesion is treated with esophageal lavage with fluid containing recombinant activated factor seven or similar activated coagulation factors or local placement in the esophagus of biodegradable sponge and or foam impregnated with recombinant activated factor seven or similar activated coagulation factors or aerosol spray or spray of a powder formulation with recombinant activated factor seven or similar activated coagulation factors or treated with an insufflated balloon with a surface impregnated with recombinant activated factor seven or similar activated coagulation factors. A dose of FVIIa of 10-50 µg/kg bodyweight per treatment or more is used until hemostasis. The treatment may be repeated 2-3 times or more with intervals of 20-30 minutes or more Example 6

A patient with hematuria due to urinary bladder bleeding occurring either spontaneous or secondary to instrumentation or resection of urinary bladder papilomas is treated with trans-urethral bladder instillation with fluid containing recombinant activated factor seven or similar activated coagulation factors or local placement into the urinary bladder of biodegradable sponge or foam impregnated with recombinant activated factor seven or similar activated coagulation factors. The dose of FVIIa per treatment is 10-50 µg/kg bodyweight or more dissolved in 100-200 ml isotonic sterile saline or more. When using an instillation of the drug the outlet from the bladder is stopped for 10-20 minutes or more to let the FVIIa exercise its fully hemostatic effect. The treatment may be repeated 2-3 times or more until hemostasis is obtained.

Example 7

A patient with nose bleeding (epistaxis) is treated with intranasal placement of packing impregnated with fluid containing recombinant activated factor seven or similar activated coagulation factors or local placement of a biodegradable sponge or foam impregnated with recombinant activated factor seven or similar activated coagulation factors or local aerosol spray or spray of a powder formulation with recombinant activated factor seven or similar activated coagulation factors. The dose of FVIIa per treatment is 10-25 µg/kg bodyweight or more. The treatment may be applied 2-3 times until hemostasis is obtained.

Example 8

A patient with local bleeding during retropubic prostatectomy or total prostatectomy is treated with lavage with isotonic sterile saline containing FVIIa or local placement in situ of the resected prostate of a biodegradable sponge and or foam impregnated with recombinant activated factor seven or similar activated coagulation factors or aerosol spray or spray of a powder formulation with recombinant activated factor seven or similar activated coagulation factors or packing with serviettes impregnated with recombinant activated factor seven or similar activated coagulation factors. The dose of FVIIa is 10-50 µg/kg bodyweight or more. The treatment may be repeated 2-3 times or more until hemostasis is obtained.

Example 9

A patient with bleeding during and or after transurethral prostatectomy is treated with uretroscopically administered lavage or irrigation with fluid containing FVIIa or local placement in situ of the resected prostate of a biodegradable sponge and or foam impregnated with recombinant activated factor seven or similar activated coagulation factors or aerosol spray or spray of a powder formulation with recombinant activated factor seven or similar activated coagulation factors or packing with serviettes impregnated with recombinant activated factor seven or similar activated coagulation factors. The dose of FVIIa is 10-50 µg/kg bodyweight or more. The treatment may be repeated 2-3 times or more until hemostasis is obtained.

Example 10

A patient undergoing hip alloplastic replacement surgery or hip or knee surgery with bleeding is treated with administration into the cavities in the acetabulum and proximal femurshaft or in distal femur and proximal crus, prepared for the insertion of the alloplastic artificial hip or knee joint is treated with lavage with fluid containing FVIIa or local placement of a biodegradable sponge and or foam impregnated with recombinant activated factor seven or similar activated coagulation factors or aerosol spray or spray of a powder formulation with recombinant activated factor seven or similar activated coagulation factors or packing with serviettes impregnated with recombinant activated factor seven or similar activated coagulation factors. The dose of FVIIa is 10-50 µg/kg bodyweight or more. The treatment may be repeated 2-3 times or more until hemostasis is obtained.

Example 11

A patient undergoing liver resection with oozing from the resected raw cut liver surface is treated with lavage with fluid containing recombinant activated factor seven or similar activated coagulation factors or local placement of a biodegradable sponge and or foam impregnated with recombinant activated factor seven or similar activated coagulation factors or aerosol spray or spray of a powder formulation with recombinant activated factor seven or similar activated coagulation factors or packing with serviettes impregnated with recombinant activated factor seven or similar activated coagulation factors. The dose of FVIIa is 25-50 µg/kg bodyweight per treatment or more. The treatment may be repeated 2-3 times or more until hemostasis is obtained.

Example 12

A patient with liver rupture is prophylactically treated or just treated with lavage with fluid containing FVIIa or local placement of a biodegradable sponge and or foam impregnated with recombinant activated factor seven or similar activated coagulation factors or aerosol spray or spray of a powder formulation with FVIIa or packing with serviettes impregnated with FVIIa. The dose of FVIIa is 25-50 µg/kg body-weight per treatment or more. The treatment may be repeated 2-3 times or more until hemostasis is obtained.

Example 13

A patient is undergoing thoracotomy due to pleuritis with perioperative decortication of the pleura parietal. Hemostasis induced by the surgical procedure is obtained using FVIIa administered during surgery as a lavage directly into the open thorax in a dose of 20 to 50 µg/kg body weight or more dissolved in sterile isotonic saline in a volume of 100 to 500 ml or more per dose. The treatment may be repeated twice or more until primary hemostasis is obtained with 30 minutes intervals. FVIIa is also used postoperatively where FVIIa may be administered via a transthoracic pleural catheter from 1 to 3 times or more depending on hemostatic response, where each dose is 10-20 µg/kg body weight or more. The dose is typically dissolved in sterile isotonic saline in a volume of 20 to 50 ml or more per dose. The FVIIa therapy may be repeated with 30 minutes intervals Example 14

In the examples 1-13 a patch may be used instead of the sponge.

The invention claimed is:

1. A method for treatment or reducing risk of intrauterine bleeding in a subject in need thereof comprising administering to the subject by local intrauterine administration an amount of about 0.1 µg to about 5.0 mg per kg bodyweight per administration of activated blood coagulation factor VIIa (FVIIa) or a biologically active variant thereof having greater than 90% sequence identity to human FVIIa, wherein the intrauterine bleeding is selected from the group consisting of postpartum hemorrhage, hemorrhage following cesarean section, anovulation uterine hemorrhage, menopausal hemorrhage, post-menopausal hemorrhage and perioperative hemorrhage.

2. The method of claim 1 wherein the intrauterine bleeding is postpartum hemorrhage.

3. The method of claim 2 wherein the postpartum hemorrhage is caused by or associated with retention of membranes and/or cotyledons.

4. The method of claim 2 wherein the postpartum hemorrhage is caused by or associated with endometritis.

5. The method of claim 2 wherein the postpartum hemorrhage is caused by or associated with uterine fibroids and/or uterine malformations.

6. The method of claim 1, wherein the intrauterine bleeding is anovulation uterine hemorrhage.

7. The method of claim 1, wherein the anovulation uterine hemorrhage is juvenile anovulation uterine hemorrhage.

8. The method of claim 1, wherein the anovulation uterine hemorrhage is caused by or associated with endometrial hyperplasia.

9. The method of claim 1, wherein the intrauterine bleeding is a menopausal hemorrhage.

10. The method of claim 1, wherein the intrauterine bleeding is a post-menopausal hemorrhage.

11. The method of claim 1, wherein the intrauterine bleeding is a perioperative hemorrhage.

12. The method of claim 11, wherein the perioperative hemorrhage is caused by or associated with hysterectomy.

13. The method of claim 11, wherein the perioperative hemorrhage is caused by or associated with radical hysterectomy.

14. The method of claim 1, wherein the radical hysterectomy is caused by or associated with lymph-node sampling and/or exairesis.

15. The method of claim 1, wherein the intrauterine bleeding is caused by or associated with a condition selected from the group consisting of first-trimester abortions, cervical ectopic pregnancy, interstitial ectopic pregnancy, second-trimester abortions, non-invasive hydatidiform mole, invasive hydatidiform mole, choriocarcinoma, third-trimester premature deliveries, third-trimester mature deliveries, placenta accreta, placenta percreta, retention of the placenta, retention of the placental cotyledon, uterine atony, amniotic embolism, hemolysis, fibrinolytic disorders, disseminated intravascular coagulation (DIC), retention of membranes, retention of cotyledons, endometritis, uterine fibroids, uterine malformations, endometrial hyperplasia, uterine fibroids, oncologic conditions or stages 3 and 4 of pelvic endometriosis.

16. The method of claim 1 wherein the factor VIIa is administered by intrauterine installation of a solution of the factor VIIa.

17. The method of claim 1, wherein the factor VIIa is administered by intrauterine lavage of a solution of the factor VIIa.

18. The method of claim 1, wherein the factor VIIa is administered by intrauterine flushing of a solution of the factor VIIa.

19. The method of claim 1, wherein the factor VIIa is administered via incision in the uterus.

20. The method of claim 1, wherein the factor VIIa is administered via a tube in the cervical channel.

21. The method of claim 1, wherein the factor VIIa is administered via the uterine cavity using a catheter.

22. The method of claim 1, wherein the factor VIIa is administered in a dose of 0.3 mg to about 3.0 mg/kg bodyweight.

23. The method of claim 1, wherein the factor VIIa is administered in a dose of 0.5 mg to about 1.5 mg/kg bodyweight.

24. The method of claim 1 wherein the factor VIIa or a biologically active variant thereof having greater than 90% sequence identity to human FVIIa is administered in the form of a spray, net, bandage, powder, sponge, granule, plaster, film, swap, gel, paste, compress or a solution comprising FVIIa or a biologically active variant thereof having greater than 90% sequence identity to human FVIIa.

* * * * *

UNITED STATES PATENT AND TRADEMARK OFFICE
CERTIFICATE OF CORRECTION

| | | |
|---|---|---|
| PATENT NO. | : 8,461,115 B2 | Page 1 of 1 |
| APPLICATION NO. | : 12/282908 | |
| DATED | : June 11, 2013 | |
| INVENTOR(S) | : Lars Otto Uttenthal | |

It is certified that error appears in the above-identified patent and that said Letters Patent is hereby corrected as shown below:

On the Title Page, please insert --Related U.S. Application Data--
At Item (60), please insert --Provisional Application No. 60/782,914, filed March 16, 2006--

In the Claims:

At Column 15, line 45, Claim 7, please delete "1"
At Column 15, line 45, Claim 7, please insert --6--

At Column 15, line 47, Claim 8, please delete "1"
At Column 15, line 47, Claim 8, please insert --6--

At Column 16, line 8, Claim 14, please delete "1"
At Column 16, line 8, Claim 14, please insert --13--

Signed and Sealed this
Twenty-seventh Day of August, 2013

Teresa Stanek Rea
*Acting Director of the United States Patent and Trademark Office*